United States Patent [19]

Sugiyama et al.

[11] Patent Number: 5,378,453
[45] Date of Patent: Jan. 3, 1995

[54] COMPOSITION FOR PREVENTING GRAYING OF THE HAIR AND RESTORING GRAYED HAIR TO ITS NATURAL COLOR

[75] Inventors: Keikichi Sugiyama, Kanagawa; Koji Takada, Fujisawa; Ikuo Yamamoto, Odawara, all of Japan

[73] Assignee: Lion Corporation, Tokyo, Japan

[21] Appl. No.: 206,675

[22] Filed: Mar. 7, 1994

Related U.S. Application Data

[60] Division of Ser. No. 53,325, Apr. 27, 1993, Pat. No. 5,318,776, which is a continuation of Ser. No. 307,549, Feb. 8, 1989, abandoned.

[30] Foreign Application Priority Data

Mar. 16, 1988 [JP] Japan ................................. 63-62821

[51] Int. Cl.$^6$ ................................................. A61K 7/06
[52] U.S. Cl. ........................................ 424/70.1; 8/405; 424/70.6
[58] Field of Search .................................. 424/70

[56] References Cited

U.S. PATENT DOCUMENTS

| | | | |
|---|---|---|---|
| 3,849,553 | 11/1974 | Dea et al. | 424/70 |
| 4,045,307 | 9/1977 | Yokota et al. | 204/64 R |
| 4,873,227 | 10/1989 | Ikada et al. | 514/47 |

FOREIGN PATENT DOCUMENTS

| | | |
|---|---|---|
| 0260697 | 3/1988 | European Pat. Off. |
| 2077725 | 5/1971 | France |
| 2139189 | 2/1973 | Germany |
| 60-174705 | 9/1985 | Japan |
| 61-165310 | 7/1986 | Japan |
| 62-63509 | 3/1987 | Japan |
| 62-63510 | 3/1987 | Japan |
| 62-45527 | 7/1987 | Japan |

OTHER PUBLICATIONS

European Search Report No. 89 10 2250, Jan. 22, 1990.

*Primary Examiner*—Thurman K. Page
*Assistant Examiner*—Jyothsna Venkat
*Attorney, Agent, or Firm*—Burns, Doane, Swecker & Mathis

[57] ABSTRACT

A composition for preventing graying of the hair and restoring grayed hair to its natural color comprises an effective amount of one member selected from the group consisting of cAMP compounds such as 8-butylthio cAMP-Na or 8-methoxy cAMP-Na and water. The composition can prevent graying of the hair and restoring grayed hair to its natural color upon application to the scalp, the effective component is very stable even in the form of compositions containing water and the composition does not cause quality deteriorations such as giving out of bad smell.

5 Claims, No Drawings

COMPOSITION FOR PREVENTING GRAYING OF THE HAIR AND RESTORING GRAYED HAIR TO ITS NATURAL COLOR

This application is a divisional of application Ser. No. 08/053,325, filed Apr. 27, 1993 now U.S. Pat. No. 5,318,776 which is a continuation of application Ser. No. 07/307,549, filed Feb. 8, 1989, now abandoned.

BACKGROUND OF THE INVENTION

The present invention relates to a composition stable in the state containing water, which, upon application to the scalp, activates melanocytes of the radix pill and promoting synthesis of melanin, thereby preventing graying of the hair and restoring grayed hair to its natural color.

Graying of the hair is a universal aging phenomenon, while hair dyes are commonly used to dye grayed hair, the use of such dyes is troublesome and sometimes causes side-effects such as rash of the scalp. Therefore, many users find hair dyes to be an unsatisfactory solution of the graying of the hair.

Under such circumstances, it has been desired to develop a pharmaceutical preparation or a cosmetic composition for application to hair capable of essentially preventing graying of the hair and restoring grayed hair to its natural color.

Heretofore, there have been some proposals such as those described in Japanese Patent Un-examined Publication (hereinafter referred to as "J. P. KOKAI") Nos. 60-174705, 61-165310, 62-45527, 62-63509 and 62-63510 in compliance with such a demand. However, the proposed techniques suffer from various disadvantages such as low effectiveness, low stability of the active components and insufficient safety. Among these, J. P. KOKAI No. 62-45527 discloses the use of adenosine 3', 5'-cyclicphosphoric acid compound (hereunder referred to as "cAMP") and derivatives thereof.

However, this method suffers from the following problems: (i) cAMP and salts thereof exhibit only a low cell membrane permeability and even if they are absorbed into cells, they are likely to be decomposed by phosphodiesterase, therefore, they do not show sufficient effect of preventing graying of the hair and restoring grayed hair to its natural color. (ii) Acyl derivatives of cAMP are unstable in a composition for use in external applications and are easily decomposed with time. Therefore, if they are used as an agent externally applied over a long period, sufficient effects cannot be expected. (iii) Moreover, the acyl derivatives of cAMP give out bad smell due to decomposition.

SUMMARY OF THE INVENTION

Accordingly, an object of the present invention is to provide a practically useful composition stable in the state containing water, which, upon application to the scalp, can prevent graying of the hair and restore grayed hair to its natural color, which does not suffer from quality deteriorations such as giving out of bad smell.

Another object of the present invention is to provide a method for preventing or treating graying of the hair and restoring grayed hair to its natural color.

The present invention has been completed on the basis of a finding that the foregoing objects of the present invention can effectively be achieved by incorporating a specific cAMP compound (derivatives) into cosmetic bases.

Consequently, the present invention provides a liquid composition for preventing graying of the hair and restoring grayed hair to its natural color, which is stable in the state containing water and which comprises one member selected from the group consisting of cAMP compounds represented by the following general formula (I) or (II):

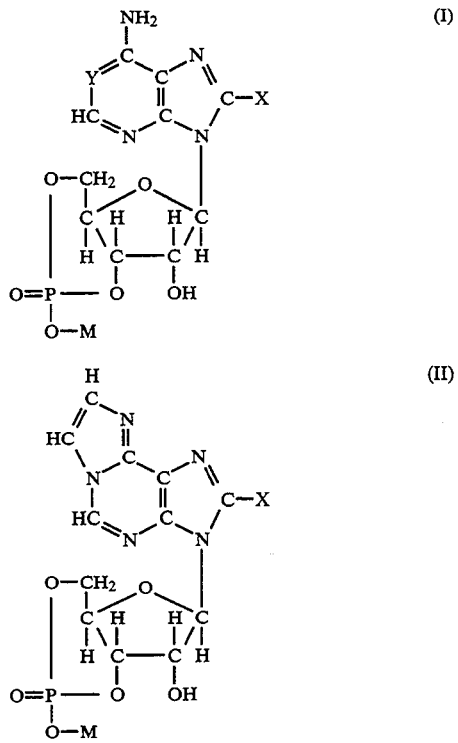

In formulas (I) and (II), X represents a hydrogen atom, a halogen atom such as a bromine, iodine, chlorine or fluorine atom; a sulfur atom-containing group such as a mercapto group, an alkylthio or hydroxyalkylthio group having 1 to 8 carbon atoms; an aromatic thio group such as a phenylthio group, a halogenated, for instance, chlorinated or brominated phenylthio group, a hydroxyphenylthio group, an alkylphenylthio or alkoxyphenylthio group whose alkyl or alkoxyl group has 1 to 6 carbon atoms or a phenylalkylenethio group for instance, a benzylthio, phenethylthio whose alkylene group has 1 to 6 carbon atoms; an oxygen atom containing group such as a hydroxyl group, an -O-alkyl group having 1 to 8 carbon atoms, an -O-phenyl group or a phenylalkyleneoxy group whose alkylene group has 1 to 6 carbon atoms; or an alkylamino group having 1 to 12, preferably 1 to 8 carbon atoms, Y represents a nitrogen atom or an N-alkyl group having 1 to 12, preferably 1 to 8 carbon atoms and M represents a hydrogen atom or a salt-forming cation, for instance, an alkali metal ion such as a sodium or potassium ion; an alkaline earth metal ion such as a calcium ion; an organic ammonium ion such as 8 triethylammonium or tributylammonium ion; or an alkanolamine group such as a monoethanolamine, diethanolamine, triethanolamine, di ethylethanolamine or dimethylethanolamine group, provided that in formula (I), X and Y do not simultaneously represent a hydrogen atom and a nitrogen atom, respectively.

In formulas (I) and (II), if X contains alkyl groups and/or Y represents N-alkyl group, the alkyl or N-alkyl group may be saturated or unsaturated, linear or blanched ones. Moreover, it may have substituent(s) such as halogen atom(s), amino group(s), nitro group(s), carboxyl group(s) and/or hydroxyl group(s) and may contain aromatic ring(s). In addition, if Y is an N-alkyl group, examples of counter ions thereof (anions) are halogen anions such as iodide or chloride ion. Intramolecular phosphate residue may serve as an anion (counter ion) for Y depending on the value of pH. In this respect, most preferred are compounds of formula (I) or (II) in which X is a hydroxyl or an -O-alkyl group, because of their low side-effects such as skin irritation and rash. Moreover, if X is a sulfur-containing group, preferred are those having an alkyl or alkylene chain adjacent to the sulfur atom from the viewpoint of influences on skin and examples thereof are alkylthio groups and benzylthio group. On the other hand, those having an aromatic ring adjacent thereto such as a phenylthio or 4-chlorophenylthio group may possibly cause side effects depending on conditions of applications.

Specific examples of the compounds of formulas (I) and (II) used in the invention include those listed in Table I as compounds Nos. 1 to 57 and those in which M is an alkali metal ion such as a sodium, lithium or potassium ion, an alkaline earth metal ion such as a calcium or magnesium ion, or an organic ammonium ion such as a triethylammonium or tributylammonium ion, which may be used alone or in combination. Examples of counter ions of compounds Nos. 37~42 and 43~49 are iodide or chloride ions or intramolecular phosphate residue depending on pH.

The cAMP compounds used in the invention can be prepared by a chemical synthesis using, as a starting material, cAMP which has been produced using fermentation techniques and synthetic methods on an industrial scale.

TABLE I

| No. | Formula | X | Y | M |
|---|---|---|---|---|
| 1 | (I) | Br | N | H |
| 2 | (I) | I | N | H |
| 3 | (I) | Cl | N | H |
| 4 | (I) | F | N | H |
| 5 | (I) | SH | N | H |
| 6 | (I) | $SCH_3$ | N | H |
| 7 | (I) | $SC_2H_5$ | N | H |
| 8 | (I) | $SC_4H_9$ | N | H |
| 9 | (I) | $SC_6H_{13}$ | N | H |
| 10 | (I) | $SC_8H_{17}$ | N | H |
| 11 | (I) | $SC_2H_4OH$ | N | H |
| 12 | (I) | S-Ph | N | H |
| 13 | (I) | S-Phe-Cl (o) | N | H |
| 14 | (I) | S-Phe-Cl (m) | N | H |
| 15 | (I) | S-Phe-Cl (p) | N | H |
| 16 | (I) | S-Phe-Br (p) | N | H |
| 17 | (I) | S-Phe-OH (p) | N | H |
| 18 | (I) | S-Phe-$OCH_3$ (P) | N | H |
| 19 | (I) | S-Phe-$CH_3$ (p) | N | H |
| 20 | (I) | $SCH_2$-Ph | N | H |
| 21 | (I) | $SC_2H_4$-Ph | N | H |
| 22 | (I) | $SC_3H_6$-Ph | N | H |
| 23 | (I) | $SC_4H_8$-Ph | N | H |
| 24 | (I) | OH | N | H |
| 25 | (I) | $OCH_3$ | N | H |
| 26 | (I) | $OC_2H_5$ | N | H |
| 27 | (I) | $OC_3H_7$ | N | H |
| 28 | (I) | $OC_4H_9$ | N | H |
| 29 | (I) | $OC_6H_{13}$ | N | H |
| 30 | (I) | $OC_8H_{17}$ | N | H |
| 31 | (I) | O-Ph | N | H |
| 32 | (I) | $OCH_2$-Ph | N | H |
| 33 | (I) | $NHC_3$ | N | H |
| 34 | (I) | $NHC_2H_5$ | N | H |
| 35 | (I) | $NHC_4H_9$ | N | H |
| 36 | (I) | $NHC_8H_{17}$ | N | H |
| 37 | (I) | H | $N^+$ $C_3$ | H |
| 38 | (I) | H | $N^+$ $C_2H_5$ | H |
| 39 | (I) | H | $N^+$ $C_4H_9$ | H |
| 40 | (I) | H | $N^+$ $C_8H_{17}$ | H |
| 41 | (I) | H | $N^+$ -Ph | H |
| 42 | (I) | H | $N^+$ $CH_2$-Ph | H |
| 43 | (I) | Cl | $N^+$ $CH_3$ | H |
| 44 | (I) | $SC_4H_9$ | $N^+$ $C_2H_5$ | H |
| 45 | (I) | S-Phe-Cl (p) | $N^+$ $C_4H_9$ | H |
| 46 | (I) | $SCH_2$-Ph | $N^+$ $C_8H_{17}$ | H |
| 47 | (I) | OH | $N^+$ -Ph | H |
| 48 | (I) | $OCH_3$ | $N^+$ $CH_2$-Ph | H |
| 49 | (I) | $NHC_4H_9$ | $N^+$ $CH_3$ | H |
| 50 | (II) | H | — | H |
| 51 | (II) | Cl | — | H |
| 52 | (II) | $SC_4H_9$ | — | H |
| 53 | (II) | S-Phe-Cl (p) | — | H |
| 54 | (II) | $SCH_2$-Ph | — | H |
| 55 | (II) | OH | — | H |
| 56 | (II) | $OCH_3$ | — | H |
| 57 | (II) | $NHC_4H_9$ | — | H |

*: "Ph" means a phenyl; "Phe" means a phenylene;, o, m and p represent ortho-, meta- and para-, respectively.

According to the present invention, there can be prepared a liquid, cream or gel composition containing the foregoing cAMP compounds as the essential component by dissolving the compound in water or a solvent containing water. The composition thus prepared is directly applied to the scalp, and thereby an excellent effect of preventing graying of the hair and restoring grayed hair to its natural color can be obtained. Moreover, the composition for preventing graying of the hair and restoring grayed hair to its natural color is very stable and does not suffer from disadvantages such as giving out of bad smell. The essential component can be incorporated into the composition of the invention in an amount ranging from 0.01 to 2% by weight (hereunder referred to as "%" for simplicity), preferably 0.02 to 1% on the basis of the total weight of the composition. In case where the cAMP compound is dissolved in water, it is preferable to use not less than 1 part by weight of water relative to 1 part by weight of the cAMP compound. On the other hand, in case where the cAMP compound is dissolved in a solvent, a preferred solvent for practical use is a mixture of ethanol and water in the weight ratio of 1/100 to 100/1, more preferably 5/100 to 100/10. There can be also used a solvent or water / ethanol / isopropyl alcohol or a solvent of water / isopropyl alcohol.

In addition to the foregoing components, the composition of the invention may further comprise any pharmaceutical component, i.e., vitamins such as vitamin A, vitamin $B_6$, vitamin E, pantothenic acid and biotin; amino acids such as methionine, cysteine, cysteine and tyrosine; antibacterial agents such as salicylic acid, hinokitiol, resorcin, trichlorocarbanilide and isopropylmethyl phenol; hormones such as ethynylestradiol and progesterone and extracts such as those extracted from seaweeds, aloe, jujube and sesame seeds. These additional components may be added to the composition for preventing graying of the hair and restoring grayed hair to its natural color in an amount ranging from 0.001 to 3%.

Moreover, other materials commonly used in cosmetics can also be incorporated into the composition for preventing graying of the hair and restoring grayed hair to its natural color according to this invention and examples thereof are oils, surfatlanta, humectants, lower alcohols, thickening agents, antioxidants, chelating agents, agents for imparting good feeling upon application, pH-adjusting agents, preservatives, perfumes and color additives. Examples of oils are fats and oils such as olive oil, jojoba oil and hydrogenated oil; waxes such as spermsoceti, beeswax and lanolin; hydrocarbons such as liquid paraffin, ceresin and squalane; fatty acids such as stearic acid and oleic acid; alcohols such as cetanol, stearyl alcohol, lanolin alcohol and hexyl decanol; and esters such as isopropyl myristate and butyl stearate. These oils are incorporated into the composition for preventing graying of the hair and restoring grayed hair to its natural color according to this invention in an amount of 0.5 to 85%. These oils can be used alone or in combination.

Examples of surfactants include anionic surfactants such as sodium stearate, sodium cetylsulfate, polyoxyethylene lauryl ether phosphate and sodium N-acyl glutamate; cationic surfactants such as stearyldimethylbenzylammonium chloride and stearyltrimethylammonium chloride; amphoteric surfactants such as alkylaminoethylgiycine hydrochloride solutions and lecithin; and nonionic surfactants such as glycerin monostearate, sorbitan monostearate, sorbitan sesquioleate, sucrose fatty acid esters, propylene glycol monostearate, polyoxyethylene oleyl ether, polyoxyethylene lauryl ether, polyoxyethylene stearyl ether, polyoxyethylene octylphenyl ether, polyoxyethylene nonylphenyl ether, polyethylene glycol monostearate, polyoxyethylene sorbitan moropalmitate, polyoxyethylene coconut fatty acid monoethanolamide, polyoxyethylene polyoxypropylene glycol, polyoxyethylene castor oil, polyoxyethylene hydrogenated castor oil, polyoxyethylene hydrogenated castor oil isostearate, polyoxyethylene hydrogenated castor oil, monopyroglutamate monoisostearate, polyoxyethylene glyceryl monoisostearate, polyoxyethylene glyceryl triisostearate, polyoxyethylene sorbitol tetraoleate and polyoxyethylene lanolin. These surfactants may be used in the composition for preventing graying of the hair and restoring grayed hair to its natural color alone or in combination and the amount thereof falls within the range of 0.1 to 15%.

Moreover, there may be mentioned such humectants as glycerin, 1,3-butylene glycol, propylene glycol, dipropylene glycol and ethylene glycol; such lower alcohols as ethanol and isopropanol; such agents for imparting good feeling to users as l-menthol and benzyl nicotinate; such thickening agents as polyethylene glycol and sodium carboxymethyl cellulose; such antioxidants as dibutylhydroxytoluene, butylhydroxyanisole and propyl gallate; such chelating agents as disodium edetate and ethanehydroxy diphosphate; such pH-adjusting agents as citric acid, sodium citrate, boric acid, borax and disodium hydrogen phosphate; and such preservatives as methyl p-hydroxybenzoate, ethyl p-hydroxybenzoate, dehydroacetic acid, salicylic acid and benzoic acid.

In this respect, these optional components are not restricted to those specific examples listed above.

The composition for preventing graying of the hair and restoring grayed hair to its natural color according to the present invention may be prepared by appropriately admixing the foregoing essential components and optional components and may be used in any forms capable of external use such as hair tonic type alcoholic pharmaceutical preparations, hair creams, lotions, milky lotions and ointments.

The composition of the present invention can contain the essential component, the optional component and balance of water, preferably 0.1 to 98%, more preferably 1 to 95% by weight of water. The composition can also contain ethanol in an amount of 0 to 99%, preferably 0 to 95%. In case where the composition contains water and ethanol, it is preferable to use ethanol which contains water in an amount of 40 to 99%, preferably 60 to 99%.

More specifically, hair tonic type alcoholic preparations, for instance, comprise 0.01 to 2% of the aforementioned essential components, 15 to 98% of a lower alcohol, 0 to 3% of the foregoing pharmaceutical components, 0 to 15% of a humectant, 0 to 8% of a surfactant, 1 to 85% of purified water and a small amount of a perfume; hair creams, for instance, comprise 0.01 to 2% of the foregoing essential components, 20 to 80% of an oil component, 0.5 to 15% of a surfactant, 0 to 15% of a humectant, 15 to 80% of purified water and small amounts of a preservative and a perfume; and milky lotions, for instance, comprise 0.01 to 2% of the foregoing essential components, 5 to 30% of an oil component, 0.5 to 15% of a surfactant, 0 to 15% of a humerrant. 50 to 95% of purified water and small amount of a preservative and a perfume.

Although, the reason why the cAMP compounds exhibit such an excellent effect of preventing graying of the hair and restoring grayed hair to its natural color has not yet been clearly evidenced, it is assumed that, when externally applied, the melanocytes present in the bulbus pill of the scalp radix pill are activated to promote the synthesis of melanin and the resultant melanin granules are promoted to be incorporated into mother cells of the hair.

Then, the effect is estimated using model mice having grayed hair and it is found that the essential components of this invention exhibit excellent effect of promoting melanin synthesis when externally applied. Moreover, as will be shown in the following Examples, they are found to be effective for treating human hair and exhibit excellent effect for preventing graying of the hair and restoring grayed hair to its natural color. In addition, these components are extremely stable in the composition containing water, do not suffer from quality deteriorations such as giving out of bad smell and thus are of much practical use.

When the level of safety of the cAMP compounds used in the invention was checked in order to make sure, no practical problem was observed with respect to acute toxicity and skin irritation and thus a high level of safety thereof was confirmed.

Thus, in accordance with the present invention, a composition for hair capable of preventing graying of the hair and restoring grayed hair to its natural color upon externally applied to the scalp is provided. Besides, the composition is extremely stable in the state containing water.

Therefore, the composition of the present invention can be widely used in various forms capable of being externally applied. Such forms include, for instance, toilet water, hair tonic type alcoholic preparations, hair creams, lotions, milky lotions, hair treatments, hair conditioners and ointments.

Moreover, those in the liquid forms may be charged into a pressure container together with a propellant, carbon dioxide, oxygen gas, LPG or the like commonly utilized.

The composition of the present invention will hereinafter be explained in more detail with reference to the following non-limitative working Examples and the effects practically achieved by the present invention will also be discussed in comparison with Comparative Examples.

EXAMPLE 1

It is known that stress is one of the causes of graying of the hair. Thus, stress is loaded to animals to obtain a state in which melanocytes are deactivated to thus causes grayed hair and during such processes, the composition for hair to which effective components of the present invention had been added was examined on what kinds of inhibitory effects to the generation of grayed hair were achieved by the composition. Moreover, the stability of the composition with time was also estimated.

The hair was removed from the back of groups each of which comprised 10 black mice and 0.1 ml of hair tonic type preparations previously prepared and which had compositions shown in Table II (containing 0.1% of each test compound) was applied to the back from which the hair was removed twice a day while intermittently stressing the test animals. One month thereafter, regenerated hair was collected from a constant area and the rate (%) of generated grayed hair to all the number of hair collected was estimated. In addition, the aforementioned hair tonic type preparations were allowed to stand at 30° C. for 3 months and the residual amount of the test compounds therein was examined by liquid chromatography as well as the degree of change in smell was also evaluated by means of sensory test. The results obtained are summarized in Table III given below.

In this connection, the results of sensory test are shown in the following 4-stage evaluation:

⊚: no deterioration (practically applicable)
○: almost no deterioration (practically applicable)
Δ: deterioration in some degree (practically inapplicable)
X: deterioration in great degree (practically inapplicable)

TABLE II

| Component | Amount Incorporated (wt %) |
| --- | --- |
| Test compound | 0.1 |
| Ethanol | 85.0 |
| Polyethylene glycol 200 | 2.0 |
| Purified water | balance |

TABLE III

| Compound to be Tested | | | Stability | |
| --- | --- | --- | --- | --- |
| Name | No. in Table I | Rate of Grayed Hair (%) | Residue (%) | S.E. |
| None (control) | — | 16.5 | — | ⊚ |
| cAMP | — | 13.2 | 96.3 | ○ |
| $N^6,O^{2'}$-dibutyryl cAMP | — | 9.1 | 86.4 | X |
| 8-fluoro cAMP | 4 | 7.6 | 99.5 | ⊚ |
| 8-methylthio cAMP | 6 | 8.0 | 99.9 | ⊚ |
| 8-phenylthio cAMP | 12 | 7.1 | 100.0 | ⊚ |
| 8-benzylthio cAMP | 20 | 7.2 | 100.0 | ⊚ |
| 8-methoxy cAMP | 25 | 7.8 | 99.7 | ⊚ |
| 1-methyl cAMP | 37 | 8.2 | 99.6 | ⊚ |

TABLE III-continued

| Compound to be Tested | | | Stability | |
| --- | --- | --- | --- | --- |
| Name | No. in Table I | Rate of Grayed Hair (%) | Residue (%) | S.E. |
| 1,$N^6$-etheno cAMP | 50 | 7.5 | 99.8 | ⊚ |

S.E.: Sensory Evaluation.

As seen from the results shown in Table III, cAMP (Comp. Ex.) is relatively excellent in stability, but shows weak effect of inhibiting generation of grayed hair. In addition, $N^6,O^{2'}$-dibutyryl cAMP (Comp. Ex.) which is a typical acyl derivative of cAMP exhibits the grayed hair inhibitory effect, but it has low stability, in other words it causes high deterioration in smell. On the contrary, the derivatives used in the composition of the present invention show not only remarkable effect of preventing the generation of grayed hair but high stability.

The foregoing results indicate that the effective components of the present invention make it possible to prevent graying of the hair and to restore grayed hair to its natural color due to the inhibition of deactivation of melanocytes or the activation of deactivated melanocytes.

The results further indicate that the effective components of the present invention are very stable and they do not cause quality deterioration such as giving out of bad smell, even when they are used as a composition for hair for a long time.

EXAMPLE 2

Hair tonic type compositions for preventing graying of the hair and restoring grayed hair to its natural color containing 0.05% of a compound to be tested were prepared and, as in Example 1, 0.1 ml each of the compositions was applied to the back of black mice, from which the hair had been removed, twice a day while stressing the mice intermittently.

One month thereafter, regenerated hair was collected from a constant area and the rate, (%) of generated grayed hair to all the number of hair collected was estimated. In addition, the aforementioned compositions were allowed to stand at 30° C. for 3 months and the residual amount of the test compounds therein was examined by liquid chromatography as well as the degree of change in smell was also evaluated by sensory test. The compositions were listed in Table IV and the results obtained are summarized in Table V given below. In this Example, the standard of sensory test is the same as in Example 1. In addition, the abbreviation $\overline{P}$ means the averaged added molar number of ethylene oxide residues.

TABLE IV

| Component | Amount Incorporated (wt %) |
| --- | --- |
| Test compound | 0.05 |
| Ethanol (95 (v/v) %) | 30.0 |
| Polyoxyethylene stearyl ether ($\overline{P} = 10$) | 2.0 |
| Perfume | small amount |
| Purified water | balance |

TABLE V

| Compound to be Tested | Rate of Grayed Hair (%) | Stability Residue (%) | S.E. |
|---|---|---|---|
| None (control) | 17.1 | — | ◉ |
| cAMP-Na | 14.0 | 97.1 | ○ |
| $N^6,O^{2'}$-dibutyryl cAMP-Na | 8.8 | 84.5 | X |
| 8-butylthio cAMP-Na (Na salt of compound No. 8 in Table 1) | 6.5 | 99.9 | ◉ |
| 8-ethylhydroxythio cAMP-NA (Na salt of compound No. 11 in Table I) | 5.5 | 99.6 | ◉ |
| 8-(4-chlorophenylthio) cAMP-Na (Na salt of compound No. 15 in Table 1) | 6.0 | 99.9 | ◉ |
| 8-hydroxy cAMP-Na (Na salt of compound No. 24 in Table I) | 5.6 | 99.7 | ◉ |
| 8-methoxy cAMP-Na (Na salt of compound No. 25 in Table I) | 4.5 | 99.9 | ◉ |
| 8-ethoxy cAMP-Na (Na salt of compound No. 26 in Table I) | 5.3 | 99.8 | ◉ |
| 8-butoxy cAMP-Na (Na salt of compound No. 28 in Table I) | 6.0 | 99.9 | ◉ |
| 8-butylamino cAMP-Na (Na salt of compound No. 35 in Table I) | 7.1 | 99.5 | ◉ |

As seen from the results listed in Table V, sodium salt of cAMP exhibits only a weak effect of inhibiting the generation of grayed of the hair. Moreover, sodium salt of $N^6,O^{2'}$-dibutyryl cAMP exhibits the aforementioned effect, but has low stability and causes substantial deterioration in smell. On the contrary, the derivatives of cARP used in the present invention show excellent effect of preventing graying of the hair and excellent stability.

The foregoing results clearly indicate that the compositions for hair to which the effective components according to the invention are added show excellent effect of preventing graying of the hair and restoring grayed hair to its natural color and is also excellent in stability. Therefore, the composition of the invention is thought to be of much practical use.

EXAMPLE 3

To component 1 (ethanol) listed in Table VI there were added components 2 to 7 to uniformly dissolve the components. On the other hand, component 8 or 9 was added to component 10 and was uniformly dissolved to form a solution followed by adding the foregoing ethanol solution (components 1 to 7) to obtain a hair tonic type composition for preventing graying of the hair. In Table VI, numerical values mean the amount of each component incorporated into the composition expressed in % by weight (these in the following Tables are shown in the same way also).

TABLE VI

| Component | Present Inv. | Comp. Ex. 1 | Comp. Ex. 2 |
|---|---|---|---|
| 1. Ethanol | 50.0 | 50.0 | 50.0 |
| 2. Propylene glycol | 2.0 | 2.0 | 2.0 |
| 3. l-menthol | 0.1 | 0.1 | 0.1 |
| 4. Biotin | 0.01 | 0.01 | 0.01 |
| 5. Polyoxyethylene octylphenyl ether (P = 5) | 0.3 | 0.3 | 0.3 |
| 6. Polyoxyethylene hydrogenated caster oil monopyroglutamate monopyroglutamate monoisostearate (P = 40) | 3.0 | 3.0 | 3.0 |
| 7. Perfume | S. A. | S. A. | S. A. |
| 8. 8-methoxy cAMP-Na (Na salt of compound No. 25 in Table 1) | 0.1 | — | — |
| 9. $N^6,O^{2'}$-dibutyryl cAMP-Na | — | 0.1 | — |
| 10. Purified water | balance | balance | balance |

S.A. means "small amount".

The composition for preventing graying of the hair thus prepared was allowed to stand at 30° C. for 3 months to determine the stability thereof and the results observed were summarized in Table VII given below.

TABLE VII

| Stability | Present Inv. | Comp. Ex. 1 | Comp. Ex. 2 |
|---|---|---|---|
| Residue (%) | 99.9 | 82.7 | — |
| Sensoty Test | ◉ | X | ◉ |

From the results shown in Table VII, It is found that the composition for preventing graying of the hair is stable and does not cause deterioration in smell while that of Comp. Ex. 1 causes substantial deterioration in smell.

Then, the compositions for preventing graying of the hair (Sample I of the present invention and Sample II of Comp. Ex. 2) were separately applied to tile scalp of a group of 20 men (40 to 60 years old) having grayed hair in accordance with Half-Head technique wherein Sample I and Sample II were separately applied to the right half of the scalp and the left half thereof in the manner twice a day (in the morning and at night) for 3 months. Then, the effects of preventing graying of the hair and restoring grayed hair to its natural color were evaluated by comparing the conditions of the portions observed before and after the application of Samples and the results obtained were listed In the following Table VIII.

TABLE VIII

| Sample I is better | Sample I is somewhat better | Same | Sample II is somewhat better | Sample II is better |
|---|---|---|---|---|
| 9 | 9 | 2 | 0 | 0 |

The results listed in Table VIII clearly indicate that the composition for preventing graying of the hair according to this invention containing 8-methoxy cAMP-Na makes it possible to reduce the amount of grayed hair and thus shows remarkable effects of preventing graying of the hair and restoring grayed hair to its natural color, comparing with the comparative composition which does not contain such an effective component (Sample II).

In addition, during and after the application of the composition for hair according to the present invention for 3 months, no abnormality was observed in the condition of the scalp.

EXAMPLE 4

Components 1 to 4 and components 5 to 10 listed in Table IX were separately heated to 80° C. to dissolve the components, then these solutions were mixed and emulsified, followed by adding component 11 during cooling the emulsion and dispersing the emulsion uniformly to obtain a milky lotion for hair.

TABLE IX

| Component | Present Inv. | Comp. Ex. I | Comp. Ex. II |
|---|---|---|---|
| 1. Lanolin alcohol | 5.0 | 5.0 | 5.0 |
| 2. Isopropyl Palmitate | 2.0 | 2.0 | 2.0 |
| 3. Stearic acid | 5.0 | 5.0 | 5.0 |
| 4. Sorbitan monostearate | 1.0 | 1.0 | 1.0 |
| 5. Triethanolamine | 1.0 | 1.0 | 1.0 |
| 6. Propylene glycol | 5.0 | 5.0 | 5.0 |
| 7. 1,$N^6$-etheno cAMP-K (K salt of compound No. 50 in Table 1) | 0.5 | — | — |
| 8. $N^6,O^{2'}$-dibutyryl cAMP-Na | — | 0.5 | — |
| 9. Methyl p-hydroxybenzoate | S.A. | S.A. | S.A. |
| 10. Purified water | balance | balance | balance |
| 11. Perfume | S.A. | S.A. | S.A. |

*: S.A. means "small amount".

The milky lotions thus prepared were allowed to stand at 30° C. for 3 months to examine the stability thereof in accordance with the same manner as in Example 1 and the results observed were summarized in the following Table X.

TABLE X

| Stability | Present Inv. | Comp. Ex. I | Comp. Ex. II |
|---|---|---|---|
| Residue (%) | 99.6 | 85.3 | — |
| Sensory Test | ⊚ | X | ⊚ |

From the results shown in Table X, it is found that the milky lotion of the present invention is stable and does not cause deterioration in smell while that of Comp. Ex. I causes extreme deterioration in smell.

Then, the effectiveness of the milky lotion of the invention and that of Comp. Ex. II was examined in the same manner as in Example 3. The results obtained are listed in Table XI given below.

TABLE XI

| Sample I is better | Sample I is somewhat better | Same | Sample II is somewhat better | Sample II is better |
|---|---|---|---|---|
| 10 | 7 | 3 | 0 | 0 |

The results listed in Table XI clearly indicate that the milky lotion according to this invention containing 1,$N^6$-etheno cAMP-K (Sample I) makes it possible to reduce the amount of grayed hair and thus shows remarkable effects of preventing graying of the hair and restoring grayed hair to its natural color, comparing with the comparative composition which does not contain such an effective component (Sample II).

In addition, during and after the application of the milky lotion according to the present invention for 3 months, no abnormality was observed in the condition of the scalp.

EXAMPLE 5

Components 1 to 6 and components 7 to 11 were separately heated to 80° C. to dissolve these and then mixed together and emulsified to form an emulsion followed by adding component 12 during cooling the emulsion and uniformly dispersing the emulsion to obtain hair creams having compositions shown in Table XII below. In Table XII, P means the averaged added molar number of ethylene oxide.

TABLE XII

| Component | Present Inv. | Comp. Ex. I | Comp. Ex. II |
|---|---|---|---|
| 1. Lanolin | 2.0 | 2.0 | 2.0 |
| 2. Glycerin monostearate | 5.5 | 5.5 | 5.5 |
| 3. Polyoxyethylene sorbitan monostearate (P = 20) | 2.0 | 2.0 | 2.0 |
| 4. Bees wax | 8.0 | 8.0 | 8.0 |
| 5. Liquid paraffin | 25.0 | 25.0 | 25.0 |
| 6. Hydrogenated oil | 23.0 | 23.0 | 23.0 |
| 7. Ethyl p-hydroxybenzoate | S.A. | S.A. | S.A. |
| 8. Borax | 0.5 | 0.5 | 0.5 |
| 9. 1-methyl cAMP-triethylammonium (triethylammonium salt of Compound No. 37 in Table I) | 1.0 | — | — |
| 10. $N^6,O^{2'}$-dibutyryl cAMP-Na | — | 1.0 | — |
| 11. Purified water | balance | balance | balance |
| 12. Perfume | S.A. | S.A. | S.A. |

*: S.A. means "small amount".

The hair creams thus prepared were allowed to stand at 30° C. for 3 months to examine the stability thereof in accordance with the same manner as in Example 1 and the results observed were summarized in the following Table XIII.

TABLE XIII

| Stability | Present Inv. | Comp. Ex. I | Comp. Ex. II |
|---|---|---|---|
| Residue (%) | 99.3 | 84.7 | — |
| Sensory Test | ⊚ | X | ⊚ |

From the results shown in Table XIII, it is found that the hair cream of the present invention is stable and does not cause deterioration in smell while that of Comp. Ex. I causes substantial deterioration in smell.

Then, the effectiveness of the hair cream of the invention and that of Comp. Ex. II was examined in the same manner as in Example 3. The results obtained are listed in Table XIV given below.

TABLE XIV

| Sample I is better | Sample I is somewhat better | Same | Sample II is somewhat better | Sample II is better |
|---|---|---|---|---|
| 9 | 8 | 3 | 0 | 0 |

The results listed in Table XIV clearly indicate that the hair cream according to this invention containing 1-methyl cAMP triethylammonium (Sample I) makes it possible to reduce the amount of grayed hair and thus shows remarkable effects of preventing graying of the hair and restoring grayed hair to its natural color, comparing with the comparative composition which does not contain such an effective component (Sample II).

In addition, during and after the application of the hair cream according to the present invention for 3 months, no abnormality was observed in the condition of the scalp.

EXAMPLE 6

The same procedures as in Example 3 were repeated to form hair tonic type compositions for preventing graying of the hair and restoring grayed hair to its natural color except that the following compounds were used in place of 8-methoxy cAMP-Na: 8-ethylhydroxythio cAMP-Na (Na salt of compound No. 11 in Table I); 8-benzylthio cAMP-Na (Na salt of compound No. 20 in Table I); 8-hydroxy cAMP-Na (Na salt of compound No. 24 in Table I); 8-ethoxy cAMP-Na (Na salt of compound No. 26 in Table I); or 8-butoxy cAMP-Na (Na salt of compound No. 28 in Table I) and the effectiveness thereof was evaluated as in Example 3. As a result, the same effect of preventing graying of the hair and restoring grayed hair to its natural color as in Example 3 was obtained. In addition, these compositions were all stable and did not cause quality deterioration such as giving out of bad smell.

EXAMPLE 7

The same procedures as in Example 5 were repeated to obtain hair creams except that the following effective compounds were used instead of 1-methyl cAMP-triethylammonium salt: 1-ethyl cAMP-Na (Na salt of compound No. 38 in Table I); 1-butyl cAMP-Na (Na salt of compound No. 39 in Table I); 1-octyl cAMP-Na (Na salt of compound No. 40 in Table I); 8-methylthio cAMP-Na (Na salt of compound No. 6 in Table I); 8-butylthio cAMP-Na (Na salt of compound No. 8 in Table I); 8-methylamino cAMP-Na (Na salt of compound No. 33 in Table I); 8-butylamino cAMP-Na (Na salt of compound No. 35 in Table I); or 8-chloro cAMP-Na (Na salt of compound No. 3 in Table I) and the effectiveness thereof was evaluated as in Example 3. As a result, the same effect of preventing graying of the hair and restoring grayed hair to its natural color as in Example 5 was obtained. In addition, either of these compositions was stable and did not cause quality deterioration such as giving out of bad smell.

What is claimed is:

1. A method for restoring grayed human hair to its natural color, comprising applying to the scalp an effective amount of a solution comprising:

(i) a compound selected from the group consisting of adenosine 3', 5'-cyclicphosphoric acid compounds having the following formula (I) or (II):

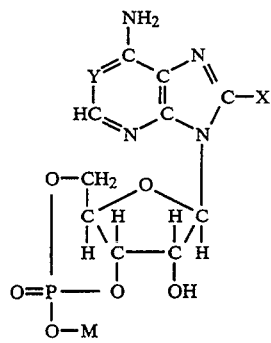

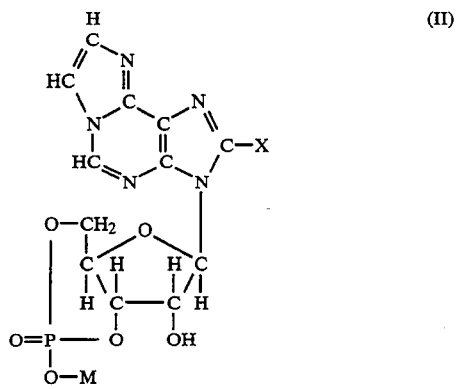

wherein X in formula (I) represents a hydroxyl group, an O-alkyl group having 1 to 8 carbon atoms; an O-phenyl group or phenylalkyleneoxy group whose alkylene group has 1 to 6 carbon X in formula (II) represents a hydrogen atom, a halogen atom, an alkylthio group having 1 to 8 carbon atoms, a benzylthio group, a hydroxyl group, an O-alkyl group having 1 to 8 carbon atoms and an alkylamino group having 1 to 12 carbon atoms, Y represents a nitrogen atom or N-alkyl group having 1 to 12 carbon atoms in which counter ion thereof is a halogen ion, and M represents a hydrogen atom or a salt-forming cation, and (ii) water, said compound being present in an amount effective to restore grayed hair to its natural color upon application to the scalp.

2. The method of claim 1 wherein X in formula (I) represents an O-alkyl group having 1 to 8 carbon atoms; an O-phenyl group or phenylalkyleneoxy group whose alkylene group has 1 to 6 carbon atoms.

3. The method of claim 1 wherein the amount of the compound ranges from 0.01 to 2% by weight.

4. The method of claim 1 wherein the amount of the compound ranges from 0.02 to 1% by weight.

5. The method of claim 1 wherein the solution is repeatedly applied to the scalp.

* * * * *